United States Patent [19]
Ogiso et al.

[11] Patent Number: 5,482,986
[45] Date of Patent: Jan. 9, 1996

[54] BENZOPYRAN COMPOUND AND USE OF THE SAME

[75] Inventors: Akira Ogiso, Fukuoka; Tsutami Misawa, Kanagawa; Rihoko Imai, Tokyo; Hisato Itoh, Fukuoka, all of Japan

[73] Assignee: Mitsui Toatsu Chemicals, Inc., Tokyo, Japan

[21] Appl. No.: 272,829

[22] Filed: Jul. 11, 1994

[30] Foreign Application Priority Data

Jul. 22, 1993 [JP] Japan .................................. 5-181098

[51] Int. Cl.⁶ .................................................... C08K 5/15
[52] U.S. Cl. ............................................................ 524/110
[58] Field of Search ............................ 549/287; 524/110

[56] References Cited

U.S. PATENT DOCUMENTS

| | | | |
|---|---|---|---|
| 2,170,127 | 8/1939 | Dalmer et al. | 549/287 |
| 2,686,170 | 8/1954 | Best | 524/110 |
| 4,273,715 | 6/1981 | Buckler et al. | 549/287 |
| 4,444,591 | 4/1984 | Kawai et al. | 524/110 |
| 4,511,685 | 4/1985 | Nissen et al. | 524/110 |
| 4,882,412 | 11/1989 | Weaver et al. | 528/190 |
| 4,892,922 | 1/1990 | Weaver et al. | 528/190 |
| 5,091,501 | 2/1992 | Weaver et al. | 528/220 |

FOREIGN PATENT DOCUMENTS

| | | |
|---|---|---|
| 53-98242 | 8/1978 | Japan . |
| 53-124556 | 10/1978 | Japan . |
| 63-225650 | 9/1988 | Japan . |
| 3-20353 | 1/1991 | Japan . |

OTHER PUBLICATIONS

Saraf et al., Eksp. Klin. Farmakol., 56(2), 1993 pp. 47–50 (Abstract).

Simonyan et al. Pyatigorsk. Farm. Inst., 27(7), 1993, pp.29–32. (Abstract).

Primary Examiner—Kriellon S. Morgan
Attorney, Agent, or Firm—Burns, Doane, Swecker & Mathis

[57] ABSTRACT

A 2H-1-benzopyran-2-on compound represented by the formula (1):

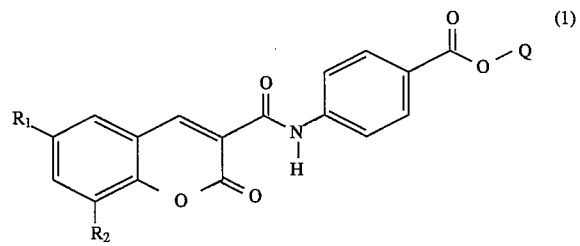

and a colorless ultraviolet absorber consisting of the compound, and a thermoplastic resin composition and formed article comprising said ultraviolet absorber. The compound can provide a thermoplastic resin composition and a formed article of the composition having excellent heat stability and sublimation resistance, comprise a non-coloring ultraviolet absorber, and are excellent in ultraviolet barrier property.

8 Claims, 2 Drawing Sheets

BENZOPYRAN COMPOUND AND USE OF THE SAME

BACKGROUND OF THE INVENTION

1. Field of the Invention

The present invention relates to an ultraviolet absorber, 2H-1-benzopyran-2-on compound which is suited for the ultraviolet absorber, and a thermoplastic resin composition and formed article thereof which comprise said ultraviolet absorber.

2. Prior Art of the Invention

Thermoplastic resins such as polyester, polymethyl methacrylate and polyvinyl chloride have excellent mechanical strengths and are widely used for films and other formed articles in view of their chemical characteristics. For example, polyester has in recent years been used in a large amount as containers of foodstuffs such as drinks, seasonings and liquors in terms of its excellent transparency, gas barrier property, and safety and hygiene. Window-sticking films have been developed for use in buildings and cars, and polyester based films in particular have been used in order to prevent window glasses from crushing and scattering in case of impact or to cut off heat radiation from outside for saving energy in air-conditioning. Further, colored polyester films having improved design have lately been marketed in view of decorative uses and have rapidly extended demand for the adhering film of window glasses which require originality for design and high performance.

On the other hand, in the field of agriculture and horticulture, thermoplastic resin films are used, for example, for growth promotion and high volume harvesting of root vegetables and other useful plants. Films based on polymethyl methacrylate and polyvinyl chloride are applied to a covering material for mulching particularly in view of light resistance, light transmittance and strength (Japanese Laid-Open Patent SHO 53-98242).

These containers and films of thermoplastic resin, for example, polyester have very excellent barrier property for ultraviolet rays of short wavelength ranging about 320 nm or less. However, ultraviolet and visible rays of long wavelength ranging about 320 nm or more mostly pass through these containers and films.

Consequently, for example, in the case of filling a fruit juice, edible oil, liquid seasoning such as "mirin" or dressing, or liquor in a polyester container and storing for several months, although there is a difference by condition of storage and by the kind of packing of foodstuffs, it often causes gradual deterioration of content, for example, delicate change in color, taste and odor. Deterioration of the content is caused by oxygen, heat, ultraviolet rays or penetration of microorganisms. Polyester containers have relatively excellent oxygen barrier property and thus prevention of deterioration of the contents can be greatly improved even under a long period of storage by further enhancing ultraviolet barrier property. Further, ultraviolet rays have been conventionally pointed out to exert a harmful influence on skin in particular. Consequently, a human body in a room can be protected by using a widow-adhering film provided with an ultraviolet barrier effect in addition to the effect on inhibiting glass scattering and cutting off heat rays.

Further, in agriculture and horticulture, mulching culture has been known to promote growth of many useful plants and to provide harvest of high quality crops in a large amount within a short period by mulching with a transparent covering material which substantially inhibits ultraviolet transmission of at least 370 nm or less (Japanese Laid-Open Patent SHO 53-124556).

At present, the industry usually conducts addition of ultraviolet absorbers in order to cut off ultraviolet rays. However, presently known ultraviolet absorbers based on hydroquinone, salicylic acid, benzophenone and benzotriazole are generally expensive compounds and require complex procedures for addition. Many absorbers are inferior in thermal stability and lead to problems such as unfavorable coloring of the resin due to thermal decomposition of the absorbers in the course of processing and embrittlement of the resin due to acceleration of cleavage in the high molecular chain of the resin. These absorbers generally sublime with ease and result in adhesion of sublimed matter on the machinery used in the steps of mixing and processing. It is also unfavorable that these absorbers are liable to migrate into the contents in the case of using the resin for containers and packaging of foodstuffs. Resins particularly comprising polyethylene terephthalate as a principal component are injection molded at very high temperatures ranging from 280° C. to 320° C. Consequently, ultraviolet absorbers used for the resin must have minimum sublimation in such temperature range.

Processes have been disclosed in order to solve these problems. For example, sublimation is reduced by using ultraviolet absorbers based on naphthalenetetracarboxylic acid, or anhydride, imide or ester thereof, or naphthalenedicarboxylic acid or derivatives thereof as described in Japanese Laid-Open Patent SHO 63-225650. In another process, a uniform composition is prepared by directly adding naphthalenetetracarboxylic acid or anhydride, imide or ester thereof, or naphthalenedicarboxylic acid or derivatives thereof to a preparation vessel of polybutylene terephthalate resin, and the uniform composition is successively blended with polyethylene terephthalate resin as described in Japanese Laid-Open Patent HEI 3-20353. However, the container or film comprising the composition of Japanese Laid-Open Patent SHO 63-225650 has a strong tendency to color yellow and has not been fully satisfactory to a packaging material of colorless and transparent content such as drinks and liquor. In the preparation process of formed articles in Japanese Laid-Open Patent HEI 3-20353, yellow coloring is improved by once preparing a polybutylene terephthalate resin composition comprising ultraviolet absorbable derivatives of naphthalenetetracarboxylic acid and/or naphthalenedicarboxylic acid and successively blending the resin composition with polyethylene terephthalate resin. Consequently, preparation steps are complex and the ultraviolet barrier effect cannot be expected unless the derivatives of naphthalene tetracarboxylic acid and/or naphthalene dicarboxylic acid are directly added to the polybutylene terephthalate resin preparation vessel in order to bond these derivatives to the polymer chain. As a result, the process is not always favorable as a mass production process of resin formed articles.

U.S. Pat. Nos. 4,882,412 and 4,892,922 have proposed a process for directly adding a 2H-1-benzopyran-2-on compound having a reactive group such as hydroxy, alkoxy, acyloxy, amino or acyloxyalkylamino group on the 7-position to a preparation vessel of polyethylene terephthalate resin in order to bond the compound to the polymer chain. The polyester resin composition thus obtained causes no dissolution of the benzopyran compound into the content, has ultraviolet absorbing ability and is thus suited for use in containers and packaging films of foodstuffs.

U.S. Pat. No. 5,091,501 has proposed a new preparation process of a polyester resin composition containing a known 2H-1-benzopyran-2-on compound, which comprises integrating the preparation step of the benzopyran compound with the preparation step of polyester resin, that is, simultaneously conducting preparation of polyester resin and the benzopyran compound by directly adding o-halocinnamic acid or its ester, the raw material of the benzopyran compound, to the preparation vessel of the polyester resin.

However, the resin composition described in U.S. Pat. No. 4,882,412 cannot substantially cut off ultraviolet rays of wavelengths less than 370 nm. Light transmittance of 10% or less is observed, for example, on the light beams having a wavelengths of 250–351 nm or incident light having a wavelength of 250–371 nm, as illustrated in U.S. Pat. No. 4,882,412, Examples 98 and 99.

Consequently, in the case of filling a fruit juice, edible oil or liquor in a polyester container composed of the above resin composition, the content is inevitably deteriorated by ultraviolet rays which have transmitted the container wall. The resin compositions described in U.S. Pat. Nos. 4,882,412 and 4,892,922 show a fluorescence by irradiation of ultraviolet rays or sunlight as described, for example, in U.S. Pat. No. 4,882,412, Examples 1 and 2, and U.S. Pat. No. 4,892,922, Examples 1 and 2. Consequently, packaging materials for foodstuffs and containers for filling drinks which are prepared from the above resin composition show a fluorescence and gives unfavorable impression on the appearance.

Further, yellow coloring is shown on the resin composition obtained in U.S. Pat. Nos. 4,892,922 and 5,091,501 as described in, for example, U.S. Pat. No. 4,892,922, Example 92 and U.S. Pat. No. 5,091,501, Example 3. Consequently, desired tone cannot be obtained even though a colorant is added and the resin composition is unsuited for a material of decorative window-adhering films having ultraviolet barrier effect.

SUMMARY OF THE INVENTION

One object of the invention is to provide, in order to solve the above problems, a colorless ultraviolet absorber having excellent heat stability and very low sublimation, and further to provide a thermoplastic resin composition and formed article thereof having an excellent ultraviolet barrier property by the addition of said ultraviolet absorber to the thermoplastic resin.

As a result of an intensive investigation in order to achieve the above object, the present inventors have found a 2H-1-benzopyran-2-on compound having excellent heat stability and very low sublimation. Thus, the present invention has been completed.

That is, one aspect of the invention is a 2H-1-benzopyran-2-on compound represented by the formula (1):

wherein $R_1$ and $R_2$ are individually a hydrogen atom or a halogen atom, and Q is a hydrogen atom or a 1~8 carbon alkyl group which may be substituted with halogen atom and/or alkoxy group. In other aspects, there are provided, a colorless ultraviolet absorber consisting of said benzopyran compound, and a thermoplastic resin composition and formed article thereof comprising said ultraviolet absorber.

The ultraviolet absorber of the invention is colorless and excellent in heat stability and sublimation resistance. A thermoplastic resin composition having an excellent ultraviolet barrier property can be prepared by addition of said ultraviolet absorber to the thermoplastic resin.

The thermoplastic resin composition of the invention comprises substantially cutting off ultraviolet rays having a longer wavelength by addition of one or more ultraviolet absorbers consisting a 2H-1-benzopyran-2-on compound to the thermoplastic resin composition in an effective amount for cutting off ultraviolet rays. The term "cut off ultraviolet rays" means to completely (almost 100%) cutting off ultraviolet rays of short wavelength, that is, at least 370 nm or less when a formed article is prepared from said resin composition.

The present invention remarkably contributes to the production of containers, films and other functional articles which require ultraviolet barrier property.

DETAILED DESCRIPTION OF THE INVENTION

In the 2H-1-benzopyran-2-on compound represented by the formula (1) in the invention, substituents $R_1$ and $R_2$ are hydrogen atom or halogen atom. Exemplary halogen atoms are fluorine, chlorine, bromine and iodine atom. The substituent Q is a 1~8 carbon alkyl group which may be substituted with halogen atom and/or alkoxy group, or a hydrogen atom. The 1~8 carbon alkyl group which may by substituted with a halogen atom or an alkoxy group includes, for example, methyl, ethyl, propyl, butyl, pentyl, hexyl, heptyl, octyl, chloroethyl, trichloroethyl, bromoethyl, iodoethyl, chloropropyl, brompropryl, chlorobutyl, bromobutyl, methoxyethyl, ethoxyethyl, n-propoxyethyl, isopropoxyethyl, methoxypropyl, ethoxypropyl, n-propoxypropyl, isopropoxypropyl, methoxybutyl, ethoxybutyl, n-propoxybutyl and isopropoxybutyl.

Representative examples of the 2H-1-benzopyran-2-on compounds of the formula (1) are illustrated in Table 1~4. However, the scope of the invention is, of course, not limited by these compounds.

TABLE 1

| No. | $R_1$ | $R_2$ | Q |
|---|---|---|---|
| 1 | H | H | $CH_3$ |
| 2 | F | H | $CH_3$ |
| 3 | Cl | H | $CH_3$ |
| 4 | Br | H | $CH_3$ |
| 5 | I | H | $CH_3$ |
| 6 | Cl | Cl | $CH_3$ |
| 7 | Br | Br | $CH_3$ |
| 8 | H | H | $CH_3$ |
| 9 | F | H | $CH_3$ |
| 10 | Cl | H | $CH_3$ |
| 11 | Br | H | $CH_3$ |
| 12 | I | H | $CH_3$ |

TABLE 1-continued

| No. | $R_1$ | $R_2$ | Q |
| --- | --- | --- | --- |
| 13 | Cl | Cl | $CH_3$ |
| 14 | Br | Br | $CH_3$ |
| 15 | H | H | $CH_2CH_3$ |
| 16 | F | H | $CH_2CH_3$ |
| 17 | Cl | H | $CH_2CH_3$ |
| 18 | Br | H | $CH_2CH_3$ |
| 19 | I | H | $CH_2CH_3$ |
| 20 | Cl | Cl | $CH_2CH_3$ |
| 21 | Br | Br | $CH_2CH_3$ |

TABLE 2

| No. | $R_1$ | $R_2$ | Q |
| --- | --- | --- | --- |
| 22 | H | H | $CH_2CH_2CH_3$ |
| 23 | F | H | $CH_2CH_2CH_3$ |
| 24 | Cl | H | $CH_2CH_2CH_3$ |
| 25 | Br | H | $CH_2CH_2CH_3$ |
| 26 | I | H | $CH_2CH_2CH_3$ |
| 27 | Cl | Cl | $CH_2CH_2CH_3$ |
| 28 | Br | Br | $CH_2CH_2CH_3$ |
| 29 | H | H | $CH(CH_3)2$ |
| 30 | F | H | $CH(CH_3)2$ |
| 31 | Cl | H | $CH(CH_3)2$ |
| 32 | Br | H | $CH(CH_3)2$ |
| 33 | I | H | $CH(CH_3)2$ |
| 34 | Cl | Cl | $CH(CH_3)2$ |
| 35 | Br | Br | $CH(CH_3)2$ |
| 36 | H | H | $CH_2CH_2CH_2CH_3$ |
| 37 | F | H | $CH_2CH_2CH_2CH_3$ |
| 38 | Cl | H | $CH_2CH_2CH_2CH_3$ |
| 39 | Br | H | $CH_2CH_2CH_2CH_3$ |
| 40 | I | H | $CH_2CH_2CH_2CH_3$ |
| 41 | Cl | Cl | $CH_2CH_2CH_2CH_3$ |
| 42 | Br | Br | $CH_2CH_2CH_2CH_3$ |

TABLE 3

| No. | $R_1$ | $R_2$ | Q |
| --- | --- | --- | --- |
| 43 | H | H | $CH_2CH_2CH(CH_3)_2$ |
| 44 | F | H | $CH_2CH_2CH(CH_3)_2$ |
| 45 | Cl | H | $CH_2CH_2CH(CH_3)_2$ |
| 46 | Br | H | $CH_2CH_2CH(CH_3)_2$ |
| 47 | I | H | $CH_2CH_2CH(CH_3)_2$ |
| 48 | Cl | Cl | $CH_2CH_2CH(CH_3)_2$ |
| 49 | Br | Br | $CH_2CH_2CH(CH_3)_2$ |
| 50 | H | H | $C(CH_3)_3$ |
| 51 | F | H | $C(CH_3)_3$ |
| 52 | Cl | H | $C(CH_3)_3$ |
| 53 | Br | H | $C(CH_3)_3$ |
| 54 | I | H | $C(CH_3)_3$ |
| 55 | Cl | Cl | $C(CH_3)_3$ |
| 56 | Br | Br | $C(CH_3)_3$ |
| 57 | H | H | $CH_2CH_2Cl$ |
| 58 | H | H | $CH_2CH_2Br$ |
| 59 | H | H | $CH_2CH_2OCH_3$ |
| 60 | H | H | $CH_2CH_2OCH_2CH_3$ |
| 61 | H | H | $CH_2CH_2OCH_2CH_2CH_3$ |
| 62 | H | H | $CH_2CH_2OCH(CH_3)_2$ |
| 63 | Cl | Cl | $CH_2CH_2OCH(CH_3)_2$ |

TABLE 4

| No. | $R_1$ | $R_2$ | Q |
| --- | --- | --- | --- |
| 64 | H | H | $CH_2CH_2CH_2OCH_3$ |
| 65 | Br | H | $CH_2CH_2CH_2OCH_3$ |
| 66 | Br | Br | $CH_2CH_2CH_2OCH_3$ |
| 67 | H | H | $CH_2CH_2CH_2OCH_2CH_3$ |
| 68 | H | H | $CH(CH_3)CH_2Cl$ |
| 69 | H | H | $CH_2CH_2CH_2CH_2Cl$ |

TABLE 4-continued

| No. | $R_1$ | $R_2$ | Q |
| --- | --- | --- | --- |
| 70 | H | H | $CH_2CH_2CH_2CH_2OCH_3$ |
| 71 | Cl | H | $CH_2CH_2CH_2CH_2OCH_3$ |
| 72 | F | H | $CH_2CH_2CH_2CH_2OCH_3$ |
| 73 | H | H | $CH_2CH_2CH_2CH_2OCH_2CH_3$ |
| 74 | H | H | $C_5H_{11}(n)$ |
| 75 | H | H | $C_6H_{13}(n)$ |
| 76 | Br | Br | $C_6H_{13}(n)$ |
| 77 | H | H | $C_7H_{15}(n)$ |
| 78 | H | H | $C_8H_{17}(n)$ |
| 79 | H | H | $CH_2CH(C_2H_5)C_4H_9$ |
| 80 | H | H | $CH_2CCl_3$ |

The 2H-1-benzopyran-2-on compound represented by the formula (1) in the invention is prepared by reacting the compound of the formula (2):

(2)

wherein $R_1$ and $R_2$ are the same as defined in the formula (1), with thionyl chloride in a solvent, and successively reacting the resultant intermediate compound of the for formula (3):

(3)

wherein $R_1$ and $R_2$ are the same as defined in the formula (1), with the compound of the formula (4):

(4)

wherein Q is the same as defined in the formula (1).

The compound of the formula (2) can be prepared with ease by a known process.

It has been known, for example, a process for reacting salicylaldehyde with malonic acid by using acetic acid as a condensing agent to obtain coumarin-3-carboxylic acid [C. M. Stuart, J. C. S., 49, 367 (1886)], a process for reacting various salicylaldehyde derivatives with diethyl malonate in piperidine as a solvent, treating with acid and successively conducting hydrolysis to obtain the product [E. Koevenagel, Ber, 31, 2619 (1898); E. Knoevenagel, ibid., 37, 4461 (1904)], a process for reacting various salicylic aldehyde derivatives with cyanoacetic acid in an aqueous alkali solution as a solvent and successively conducting ring closure by acid and hydrolysis to obtain the product [Haarman and Reimer, D. R. P. 189252], and a process for reacting various salicylic aldehyde derivatives with malononitrile in piperidine as a solvent, treating with acid and conducting hydrolysis to obtain the product [L. Woods and J. Sapp, J. O. C., 30, 312 (1965)].

The compounds of the formula (2) include, for example, coumarin-3-carboxylic acid, 6-fluoro-coumarin-3-carboxylic acid 6-chloro-coumarin-3carboxylic acid,
6-bromo-coumarin-3-carboxylic acid, 6-iodo-coumarin-3-carboxylic acid,
6,8-difluoro-coumarin-3-carboxylic acid,
6,8-dichloro-coumarin-3-carboxylic acid,
6,8-dibromo-coumarin-3-carboxylic acid and
6,8-diiodo-coumarin-3-carboxylic acid.

Exemplary compounds represented by the formula (4), include methyl p-aminobenzoate, ethyl p-aminobenzoate, n-propyl p-aminobenzoate, isopropyl p-aminobenzoate, n-butyl p-aminobenzoate, isobutyl p-aminobenzoate, tert-butyl p-aminobenzoate, pentyl p-aminobenzoate, 2-pentyl p-aminobenzoate, 3-pentyl p-aminobenzoate, isopentyl p-aminobenzoate, neopentyl p-aminobenzoate, hexyl p-aminobenzoate, 2-hexyl p-aminobenzoate, heptyl p-aminobenzoate, 2-heptyl p-aminobenzoate, octyl p-aminobenzoate, 2-ethylhexyl p-aminboenzoate, 2-methoxyethyl p-aminobenzoate, 2- ethoxyethyl p-aminobenzoate, 2-chloroethyl p-aminobenzoate, 2-bromoethyl p-aminobenzoate, 2,2,2-trichloroethyl p-aminobenzoate and other benzoic acid derivatives having an amino group on the p-position of an alkoxycarbonyl group which may be substitued with a halogen atom or alkoxy group.

The amount of thionyl chloride used is preferably 1~1.5 moles per mole of the overall compound of the formula (2). The amount of the benzoic acid derivatives of the formula (4) is preferably 1~1.5 moles per mole of the overall compound of the formula (2).

Preferred solvents used include N,N-dimethylimidazolidinone, sulfolane, N-methyl-2-pyrrolidone and other aprotic polar solvents; and benzene, toluene, xylene, chlorobenzene, dichlorobenzene, chloronaphthalene, nitrobenzene and other aromatic solvents. Amount of the solvents used is 1~100 parts by weight per part of the compound of the formula (2).

The reaction of the compound of the formula (2) with thionyl chloride in the solvent is preferably carried out at 0°~120° C. for 1 minute~10 hours.

The compound of the formula (3) is reacted in the solvent with the compound of the formula (4) preferably at 10°~200° C., more preferably at 40°~150° C. The reaction time is preferably 30 minutes~10 hours.

The ultraviolet absorber of the invention comprises at least one of the 2H-1-benzopyran-2-on compound obtained by the above process and can be used singly or as a mixture. The 2H-1-benzopyran-2-on compound can be used as intact in the crude state and is more preferably used after purification by recrystallization or other means of purification. The compound is also preferably used after grinding to a particle size of several microns or less. The ultraviolet absorber of the invention is colorless and can absorb ultraviolet rays of wavelength ranging at least 370 nm or less.

The thermoplastic resin composition of the invention is prepared by adding one or more ultraviolet absorbers of the invention to a thermoplastic resin in an effective amount for cutting off ultraviolet rays. The 2H-1-benzopyran-2-on compound which is the ultraviolet absorber of the invention can be added in any step of thermoplastic resin preparation, for example, before starting polycondensation reaction, in the course of polycondensation reaction, after finishing polycondensation reaction, in a granular state or in the processing step. The ultraviolet absorber of the invention can equally exert an ultraviolet barrier effect by addition in any step before processing.

A simple preferred means for preparing the thermoplastic resin composition of the invention is to add the ultraviolet absorber of the invention in a certain step before processing by using particularly a thermoplastic resin which is available with ease in the market. The ultraviolet absorber of the invention is added to the thermoplastic resin at a temperature of preferably 400° C. or less, more preferably 350° C. or less.

Alternatively, the resin composition having desired ultraviolet barrier property can be finally obtained by preparing a so-called master batch which has from several times to 100 times, practically 5~50 times the prescribed concentration of the ultraviolet absorber and diluting the master batch with a fresh thermoplastic resin.

The amount of the ultraviolet absorber of the invention, the 2H-1-benzopyran-2-on compound, can be broadly changed depending upon the kind of thermoplastic resin used and the thickness of the formed articles such as films and sheets. In order to achieve the object of the invention, that is, to render transmittance almost 0% on the ultraviolet rays having a short wavelength ranging 370 nm or less, the amount of the ultraviolet absorber is preferably 0.001 parts by weight or more for 100 parts by weight of the thermoplastic resin. On the other hand, the amount of the ultraviolet absorber of 20 parts by weight for 100 parts by weight of the resin is satisfactory to cut off ultraviolet rays of short wavelength ranging 370 nm or less. Consequently, the amount of the ultraviolet absorber is most preferably in the range of 0.01~10 parts by weight.

It has been generally known that the relationship between the amount of an ultraviolet absorber formulated and the thickness of a formed article satisfies preferably formula (5):

$$10 \leq AB \tag{5}$$

more preferably the formula (6):

$$15 \leq AB \tag{6}$$

wherein A is the amount (part by weight) of the ultraviolet absorber for 100 parts by weight of the thermoplastic resin, and B is the thickness (μm) of the formed article. Consequently, the relationship is also worthy of consideration.

Exemplary thermoplastic resins which can be used for the thermoplastic resin composition of the invention include polystyrene, polyester, polymethyl methacrylate, polycarbonate, polyether sulfone, polyamide, polyimide, polyvinyl chloride, and copolymers or mixtures thereof. Polyester, polymethyl methacrylate and polycarbonate are preferred in view of light resistance, light transmission and mechanical strength. Particularly, polyester has excellent mechanical strength and processability and is thus most preferred.

No particular restriction is imposed upon the molecular structure of the polyester used for the invention. The polyester is preferably thermoplastic. In practice, the polyester is obtained by polycondensation of one or more dicarboxylic acid components and one or more dihydric alcohol components, or by polycondensation or copolycondensation of hydroxycarboxylic acid. The dicarboxylic acid components include, for example, aromatic dicarboxylic acid such as terephthalic acid, isophthalic acid, phthalic acid, naphthalenedicarbox acid, bis- α, β-(2-chlorophenoxy)butanoic acid, diphenylenethardicarboxylic acid and their ester derivatives; alicylic dicarboxylic acid such as cyclohexane-1,4-dicarboxylic acid and their ester derivatives; aliphatic dicarboxylic acid such as succinic acid, adipic acid, sebacic acid, azelaic acid and their ester derivatives; and unsaturated dicarboxylic acid such as fumaric acid, 4-carboxyl cinnamic acid and their ester derivatives. The dihydric alcohol components include, for example, aliphatic dihydric alcohol such as ethylene glycol, diethylene glycol, propylene glycol and butanediol; alicyclic glycol such as cyclohexanedimethanol; bisphenol derivative such as bis-(4'-β-hydroxyethoxyphenyl)propane; and polyetherdiol represented by the formula(7) :

(7)

wherein l is an integer of 1~6 and n is an integer of 3 or more. Hydroxycarboxylic acids include, for example, glycolic acid, lactic acid, hydroxypropionic acid and hydroxybutyric acid. Polyglycolic acid, polylactic acid or their copolyester is obtained from these hydroxycarboxylic acids.

In these polyesters, polyethylene terephthalate, polyethylene naphthalate and polyethylene bis- α, β-(2-chlorophenoxy)ethane-4,4'-dicarboxylate are preferred in view of excellent resistance to heat and moisture. Polyethylene terephthalate and polyethylene naphthalate are most useful and preferred because of particularly excellent transparency.

The thermoplastic resin composition of the invention comprises at least 50% by weight, preferably 80% by weight or more of such polyester resin. The composition can also comprise polymethyl methacrylate, polycarbonate and other thermoplastic resins in addition to the polyester resin of the invention.

The ultraviolet absorber of the invention is colorless and does not color the thermoplastic resin. Thus, a thermoplastic resin composition having desired tone can be obtained by using a colorant. Exemplary colorants which can be used for the thermoplastic resin composition of the invention include multi-ring based heat-resistant, hydrophobic dyes, in practice, hydrophobic dyes having a skeleton which belongs to perinone, anthrapyridone, quinophthalone and anthraquinone.

These colorants have good compatibility with the thermoplastic resin, exhibit sufficient heat and color stability at the production and processing temperature of the thermoplastic resin. When the thermoplastic resin is used for packaging and containers for foodstuffs, pigments and dyes having no safety and health problems are selected. Alternatively, the resin composition having desired tone can be finally obtained by preparing a so-called master batch which has several times to 100 times, practically 5~50 times the prescribed concentration of the colorant and diluting the master batch with a non-colored or colored thermoplastic resin.

The thermoplastic resin composition of the invention having excellent ultraviolet barrier property can be processed by common melt-forming processes to manufacture useful articles.

For example, a polyester resin composition is extruded to form a sheet and successively the sheet is monoaxially or biaxially stretched to obtain a film. The film thus obtained can be most preferably used or packaging of food-stuffs and a mulching material in agriculture and horticulture. Hollow articles having ultraviolet barrier property, gas barrier property, toughness and non-colored transparency can also be prepared by blow-molding. These hollow articles are preferably used for containers of foodstuffs such as a fruit juice, edible oil, seasoning and liquor. An injection molding process can also provide non-colored, molded articles having a desired shape.

Further, the thermoplastic resin composition comprising the colorant of the invention can also be subjected to common melt processing to manufacture useful formed articles.

For example, the polyester resin composition having the desired tone is extruded to form a sheet, and successively the sheet is monoaxially or biaxially stretched to obtain a film. The film thus obtained is fitted with an adhesive layer and deposited aluminum layer to form a functional film. The functional film is suited for use in a glass scattering preventive film and a heat-ray barrier film in the field of buildings and vehicles. Injection molding can also provide molded articles having desired tones and shapes.

The invention will hereinafter be illustrated in detail by way of examples.

In these examples, part means part by weight.

Thermogravimetric analyses in the examples were carried out with a thermogravimetric analyser, model TGA-50 (manufactured by Shimadzu Seisakusho Co.) by using 3 mg of a sample at a temperature rise rate of 10° C./min.

Molar extinction coefficient of 2H-1-benzopyran-2-on compounds obtained in Examples 1 and 2 and Comparative Examples 1 and 2, respectively, was measured at a wavelength of 380 nm with a spectrometer, model UV-2200 (manufactured by Shimadzu Seisakusho Co.)

Transmittance spectrum of ultraviolet and visible radiation of films obtained in Examples 3 and 4 and Comparative Examples 3, 4 and 5, respectively, was measured in a wavelength range of 280~500 nm with the same spectrometer as above.

EXAMPLE 1

After dissolving 143 parts of coumarin-3-carboxylic acid at 25° C. in 1500 parts of dimethylimidazolidinone, the resultant solution was cooled to 5° C. To the solution, 107 parts of thionyl chloride were added at 15° C. or less to prepare a solution of coumarin-3-carbonyl chloride. The carbonyl chloride solution was heated to 140° C. while adding 150 parts of ethyl p-aminobenzoate, maintained at the temperature for 3 hours, and cooled to 25° C.

The reaction mixture was filtered and the filter cake was washed with methanol and dried. The 2H-1-benzopyran-2-on compound thus obtained was 240 parts. Melting point; 251°~252° C.

The compound was subjected to a thermogravimetric analysis.

No weight change was observed up to 249° C. Weight loss from the initial weight was 1.0% at 270° C. and 5.0% at 289° C. structural formula and maximum absorption wavelength of the compound are illustrated in Table 5.

TABLE 5

| | Structural formula | Maximum absorption wavelength λ max(nm) |
|---|---|---|
| Example 1 | [structure: coumarin-3-carboxamide with N-H linked to p-substituted phenyl bearing C(=O)OCH₂CH₃] | 338<br>308 |
| Example 2 | [structure: coumarin-3-carboxamide with N-H linked to p-substituted phenyl bearing C(=O)OCH₂CH₂CH₂CH₃] | 338<br>308 |
| Compara. Example 1 | [structure: coumarin-3-carboxamide with N-H linked to o-substituted phenyl bearing C(=O)OCH₂CH₃] | 338<br>306 |
| Compara. Example 2 | [structure: coumarin-3-carboxamide with N-H linked to m-substituted phenyl bearing C(=O)OCH₂CH₃] | 336<br>305 |

EXAMPLE 2

In 1400 parts of N-methyl-2-pyrrolidone, 143 parts of coumarin-3-carboxylic acid was dissolved at 20° C. and 107 parts of thionyl chloride was added at 35° C. or less to prepare a solution of coumarin-3-carbonyl chloride.

The solution thus obtained was heated to 150° C. while adding 174 parts of butyl p-aminobenzoate, maintained at the temperature for an hour and cooled to 25° C. The reaction mixture thus obtained was filtered, and the filter cake was washed with dimethylformamide and successively with methanol and dried.

The 2H-1-benzopyran-2-on compound obtained was 258 parts. The compound was subjected to a thermogravimetric analysis. No weight change was observed up to 263° C. The compound had a 1.0% weight loss temperature of 283° C. and a 5.0% weight loss temperature of 309 ° C.

Structural formula and maximum absorption wavelength of the compound are illustrated in Table 2.

Comparative Example 1

The same procedures as Example 1 were carried out except that 150 parts of ethyl p-aminobenzoate were replaced by 150 parts of ethyl o-aminobenzoate. The 2H-1-benzopyran-2-on compound thus obtained was 212 parts.

The compound was subjected to a thermogravimetric analysis. No weight change was observed up to 129°. The compound had a 1.0% weight loss temperature of 234° C. and a 5.0% weight loss temperature of 264° C. Structural formula and maximum absorption wavelength of the compound are illustrated in Table 5.

Comparative Example 2

The same procedures as Example 1 were carried out except that 150 parts of ethyl p-aminobenzoate were replaced by 150 parts of ethyl m-aminobenzoate. The 2H-1-benzopyran-2-on compound thus obtained was 228 parts.

The compound was subjected to a thermogravimetric analysis. No weight change was observed up to 236° C. The compound had a 1.0% weight loss temperature of 260° C. and a 5.0% weight loss temperature of 293° C.

Structural formula and maximum absorption wavelength of the compound are illustrated in Table 5.

EXAMPLE 3

To 10000 parts of polyethylene terephthalate (manufactured by UNITIKA Co.) which were previously fused at 280° C., 100 parts of the 2H-1-benzopyran-2-on compound obtained in Example 1 were added and mixed at 280° C.

The mixture obtained was extruded through an extruder having a diameter of 30 mm to prepare a thin raw sheet having a thickness of about 200 μm. Successively, the thin sheet was monoaxially stretched under fixed width at a preheating temperature of 75° C. and a stretching temperature of 90° C. by using a batch type stretching machine to obtain a transparent film having a thickness of 102 μm.

Figure 1:
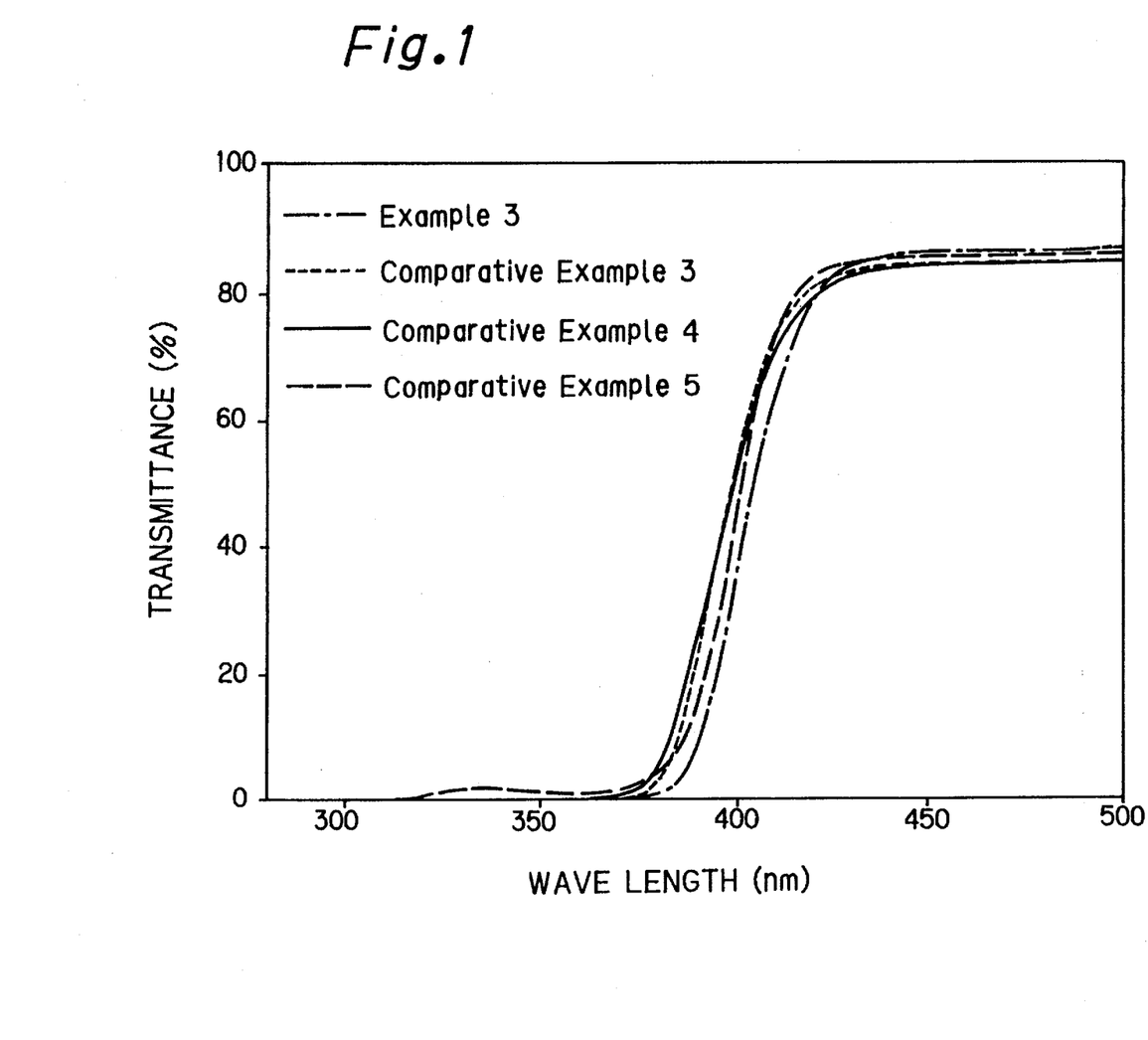
FIG. 1 illustrates ultraviolet and visible ray spectra of thermoplastic resin compositions obtained in Example 3 and Comparative Examples 3, 4 and 5.

The film had an ultraviolet transmittance of 0.0% at 370 nm and 1.1% at 380 nm. No coloring was observed on the film. Absorption spectrum of ultraviolet and visible radiation is illustrated in FIG. 1.

No deposit observed on the extruder nozzle in the preparation of the thin sheet containing the ultraviolet absorber. Sublimation of the compound was not observed.

Comparative Example 3

The same procedures as Example 3 were carried out except that 100 parts of the 2H-1-benzopyren-2-on compound of Example 1 were replaced by 100 parts of the 2H-1-benzopyran-2-on compound of Comparative Example 1. A transparent film having thickness of 134 μm was obtained. The film had an ultraviolet transmittance of 0.1% at 370 nm and 2.7% at 380 nm. No coloring was observed on the film.

Absorption spectrum of ultraviolet and visible radiation is illustrated in FIG. 1.

Comparative Example 4

The same procedures as Example 3 were carried out except that 100 parts of the 2H-1-benzopyren-2-on compound of Example 1 were replaced by 100 parts of the 2H-1-benzopyran-2-on compound of Comparative Example 2. A transparent film having thickness of 133 μm was obtained.

The film had an ultraviolet transmittance of 0.2% at 370 nm and 5.1% at 380 nm. No coloring was observed on the film.

Absorption spectrum of ultraviolet and visible radiation is illustrated in FIG. 1.

Comparative Example 5

The same procedures as Example 4 were carried out except that 100 parts of the 2H-1-benzopyren-2-on compound were replaced by 100 parts of a marketed benzotriazole based ultraviolet absorber, TINUVIN 326 (Trade Mark of Ciba Geigy Co.)[2-(3-t-butyl-5-methyl-2-hydroxyphenyl)-5-chlorobenzotriazole]. A transparent film having thickness of 103 μm was obtained.

The ultraviolet absorber TINUVIN 326 used was subjected to a thermogravimetric analysis. Weight change was observed from 167° C. Weight loss from the initial weight was 1.0% at 180° C. and 5.0% at 202° C.

The film had an ultraviolet transmittance of 0.7% at 370 nm and 3.7% at 380 nm. No coloring was observed on the film. Absorption spectrum of ultraviolet and visible radiation is illustrated in FIG. 1. In the preparation of the thin sheet by using the ultraviolet absorber, light yellow powder was adhered on the extruder nozzle and yellow deposit was gradually observed in the extruded sheet after delivering about 1 kg of the sheet.

As seen in FIG. 1, the thermoplastic resin composition of Example 3 had a transmittance of about 0% at 370 nm.

On the other hand, any of the thermoplastic compositions obtained in Comparative Examples 3, 4 and 5 had a transmittance of 0.1~0.7%, although absorptivity was enhanced by making the film thickness equal to or thicker than that of the film of Example 3. Consequently, the thermoplastic resin composition containing the 2H-1-benzopyran-2-on compound of the invention was found to have an excellent screening ability for ultraviolet radiation. Sublimation of the compound or decomposition thereof were observed.

EXAMPLE 4

To 10000 parts of polyethylene terephthalate (manufactured by UNITIKA Co.) which were previously fused at 280° C., 102 parts of the 2H-1-benzopyran-2-on compound of Example 1 and 11 parts of a red colorant Indanthrene Red FBB which was a marketed anthraquinone base vat dye were added and mixed at 280° C. The mixture obtained was extruded through an extruder having a diameter of 30 mm to prepare a thin raw sheet having a thickness of about 200 μm. Successively, the thin sheet was monoaxially stretched under fixed width at a preheating temperature of 75° C. and a stretching temperature of 90° C. by using a batch type stretching machine to obtain a transparent film having a thickness of 151 μm.

The film had an ultraviolet transmittance of 0.0% at 370 mm and 0.2% at 380 nm. Red coloring was observed on the film. Absorption spectrum of ultraviolet and visible radiation is illustrated in FIG. 2.

Figure 2:
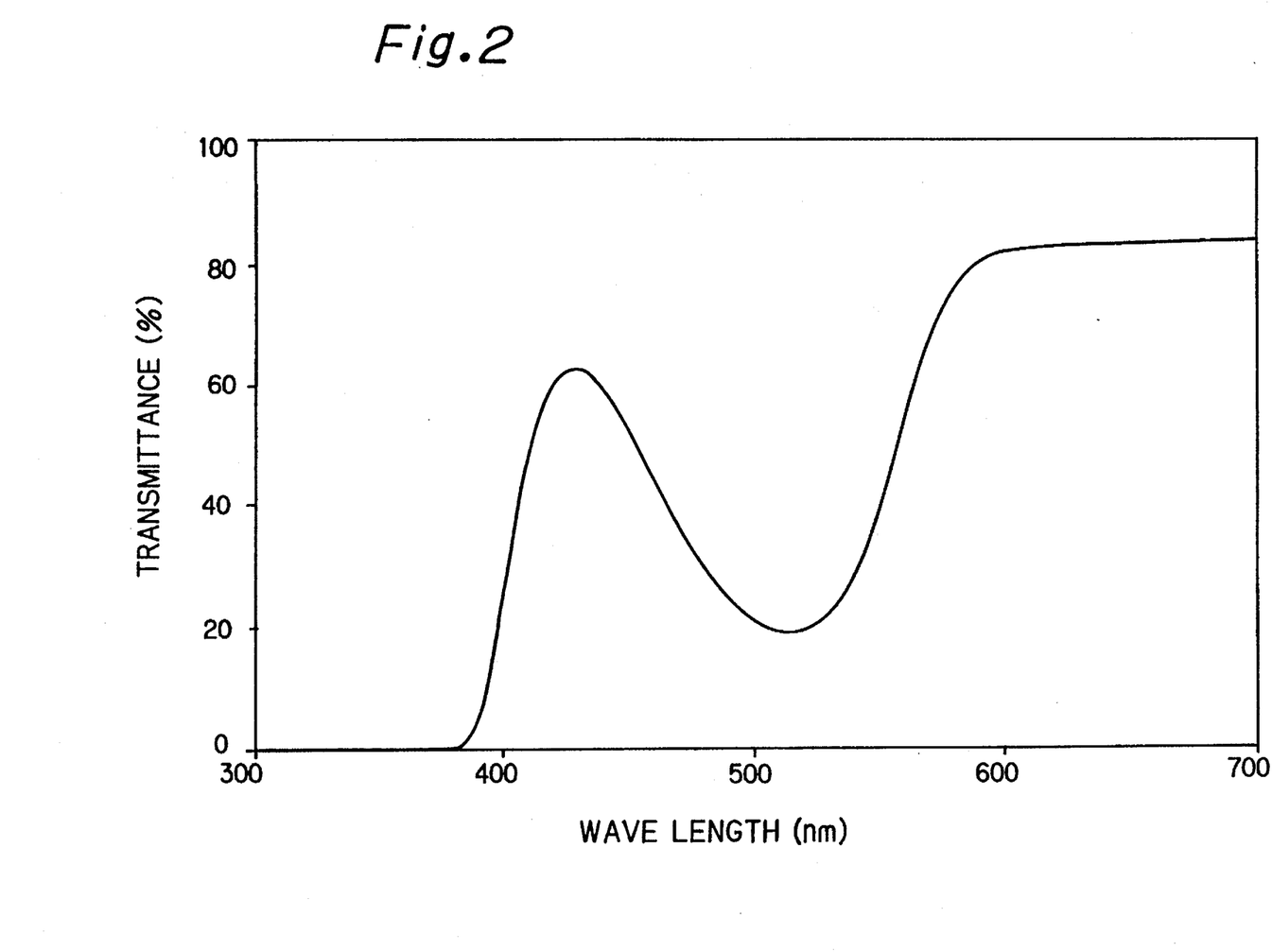
FIG. 2 illustrates ultraviolet and visible ray spectra of thermoplastic resin composition obtained in Example 4.

As seen in FIG. 2, the thermoplastic resin composition of Example 4 had an ultraviolet transmittance of 0.0% at 370 nm and 0.2% at 380 nm, and thus had an excellent screening ability for ultraviolet radiation.

In preparing the thin raw sheet by using said ultraviolet absorber, no deposit was found on the extruder nozzle.

Sublimation of the compound was not observed.

What is claimed is:

1. A thermoplastic resin composition obtained by adding at least one 2H-1-benzopyran-2-on compound represented by the formula 1:

wherein $R_1$ and $R_2$ are individually a hydrogen atom or a halogen atom, and Q is a 1~8 carbon alkyl group which may be substituted with halogen atom and/or alkoxy group, or a hydrogen atom, to a thermoplastic resin in an effective amount for cutting off ultraviolet rays.

2. A thermoplastic resin composition of claim 1 wherein the effective amount for cutting off ultra violet rays is 0.001~20 parts by weight of the ultraviolet absorber for 100 parts by weight of the thermoplastic resin.

3. A thermoplastic resin composition of claim 2 wherein the thermoplastic resin is a polyester resin.

4. A formed resin article having ultraviolet barrier property obtained by forming the thermoplastic resin composition of claim 3 into an article.

5. A thermoplastic resin composition of claim 1 wherein the thermoplastic resin is a polyester resin.

6. A formed resin article having ultraviolet barrier property obtained by forming the thermoplastic resin composition of claim 2 into an article.

7. A formed resin article having ultraviolet barrier property obtained by forming the thermoplastic resin composition of claim 1 into an article.

8. A formed resin article having ultraviolet barrier property obtained by forming the thermoplastic resin composition of claim 5 into an article.

* * * * *